(12) United States Patent
Wallace et al.

(10) Patent No.: US 8,968,253 B2
(45) Date of Patent: Mar. 3, 2015

(54) CATHETER SECUREMENT DEVICE

(71) Applicant: Centurion Medical Products Corporation, Williamston, MI (US)

(72) Inventors: Corey M. Wallace, Ann Arbor, MI (US); Tamer S. Elsamahy, Brighton, MI (US)

(73) Assignee: Centurion Medical Products Corporation, Williamston, MI (US)

( * ) Notice: Subject to any disclaimer, the term of this patent is extended or adjusted under 35 U.S.C. 154(b) by 160 days.

(21) Appl. No.: 13/795,555

(22) Filed: Mar. 12, 2013

(65) Prior Publication Data
US 2014/0276440 A1      Sep. 18, 2014

(51) Int. Cl.
*A61M 5/32* (2006.01)
*A61M 25/02* (2006.01)

(52) U.S. Cl.
CPC .................................... *A61M 25/02* (2013.01)
USPC .......................................... 604/180; 604/174

(58) Field of Classification Search
USPC ......................................... 604/174, 177–180
See application file for complete search history.

(56) References Cited

U.S. PATENT DOCUMENTS

| 4,726,716 A * | 2/1988 | McGuire ........................ 604/180 |
| 2009/0326474 A1 * | 12/2009 | Bierman et al. .............. 604/180 |

\* cited by examiner

*Primary Examiner* — Nicholas Lucchesi
*Assistant Examiner* — Leah Stohr
(74) *Attorney, Agent, or Firm* — Kristin L. Murphy; Brooks Kushman P.C.

(57) ABSTRACT

A catheter securement device includes a flexible base member having an adhesive side and an opposite non-adhesive side. A elastomeric anchoring member is mounted on the nonadhesive side of the base member. The anchoring member integrally includes a body attached to the base member, a pair of opposing pull tabs freely extending outwardly from the body, a keeper disposed in each of the pull tabs, and a T-shaped strap freely extending from the body.] The T-shaped strap terminates in a pair of opposing heads that are disposed generally parallel to the pull tabs. Pulling the opposing pull tabs opens the keepers for receiving the heads of the T-shaped strap, and the heads of the T-strap are selectively insertable into the keepers for securing a catheter between the anchoring member body and the strap.

15 Claims, 4 Drawing Sheets

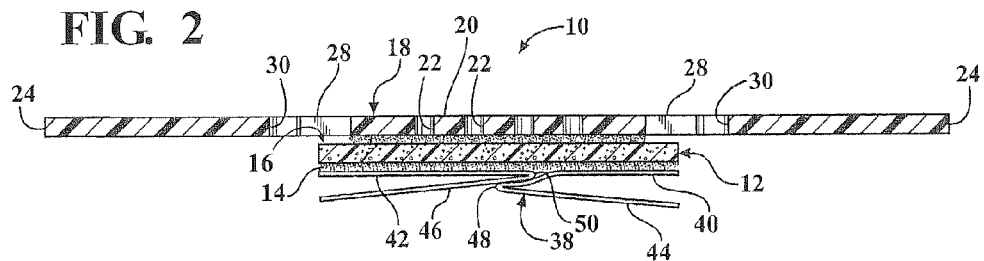
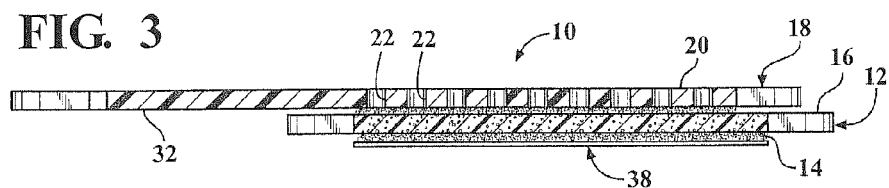
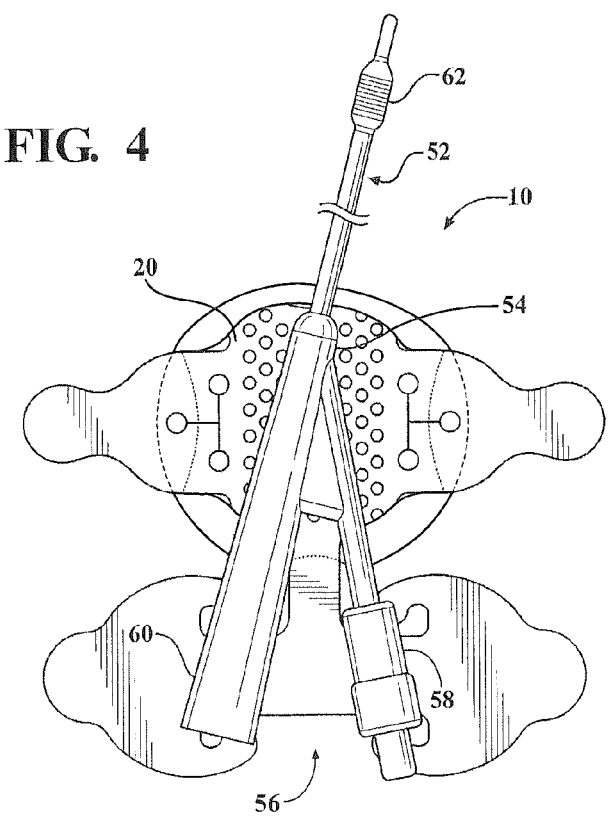

CATHETER SECUREMENT DEVICE

TECHNICAL FIELD

This disclosure relates to securement devices, for catheters and more particularly to securement devices securing catheters to a patient's skin.

BACKGROUND

It is known in the art relating to catheters that after insertion of a catheter into a catheter insertion site, the catheter must be secured to limit or prevent pulling and tugging forces from disturbing the catheter at the catheter insertion site. Commonly, surgical tape is used to hold the catheter to the patient's skin. Oftentimes, this method is ineffective to securely anchor the catheter and to prevent catheter movement. Also, the use of surgical tape can lead to complications such as decreased circulation, unwanted compression of catheter tubing, skin irritation and unnecessary tugging of the catheter during its intubation period and upon removal.

SUMMARY

In one exemplary arrangement, the present disclosure provides a catheter securement device that securely anchors a catheter to a patient's skin while at the same time is easily removed from the catheter without damaging the catheter or disturbing the catheter insertion site. The present catheter securement device is may be used to anchor a Foley catheter or any similar type catheter including a bifurcation/fork in the catheter tubing. For example, one potential use of the present catheter securement device is to secure a pediatric Foley catheter, but the catheter securement device may be used to secure any Foley catheter of any manufacturer in which the check valve is branched from the catheter tubing at a Y-fork, or a T-fork. Also, the present catheter securement device may secure any catheter tubing including a bifurcation, a trifurcation that includes for example, a triple lumen. The present catheter securement device prevents stresses applied to the catheter tubing from transferring to the catheter insertion site and causing catheter migration or removal as well as insertion site irritation. In addition, the catheter securement device may be utilized in an open or closed system.

In one exemplary arrangement, a catheter securement device includes a flexible base member having an adhesive side and an opposite non-adhesive side. A single piece elastomeric anchoring member is mounted on the non-adhesive side of the base member. The anchoring member integrally includes a body attached to the base member. A pair of opposing pull tabs freely extend outwardly from the body. A keeper is disposed in each of the pull tabs, and a T-shaped strap freely extending from the body in a direction generally perpendicular to the orientation of the pull tabs. The T-shaped strap terminates in a pair of opposing heads that are disposed generally parallel to the pull tabs. Pulling the opposing pull tabs opens the keepers for receiving the heads of the T-shaped strap. The heads are insertable into the keepers for securing a bifurcated catheter between the anchoring member body and the strap.

In one exemplary arrangement, the keeper may include a slit, and the slit may be T-shaped. The keeper also may include a circular aperture at each end of the slit.

The heads of the strap may be generally arrow-shaped. Each head may include a pair of hooks. Each hook is cooperable with the keeper to secure the head in the keeper.

The base member may extend beyond the body of the anchor member. The base member may include a pair of arms extending generally in the direction of the strap for providing additional cushioning for the bifurcated catheter.

The body of the anchoring member may include a plurality of apertures therethrough. The anchoring member may be made of a flexible, low surface energy material. The anchoring member also may be made of a breathable elastomeric material.

These and other features of the securement devices disclosed herein will be more fully understood from the following detailed description taken together with the accompanying drawings.

BRIEF DESCRIPTION OF THE DRAWINGS

FIG. 2 is a cross-sectional view of the catheter securement device taken along the line 2-2 in FIG. 1;

FIG. 3 is a cross-sectional view of the catheter securement device taken along the line 3-3 in FIG. 1;

FIG. 4 is an environmental view of the catheter securement device of FIG. 1, illustrating a method of anchoring a catheter by first placing and properly positioning the catheter securement device between the catheter and a patient's skin;

DETAILED DESCRIPTION

Figure 1:
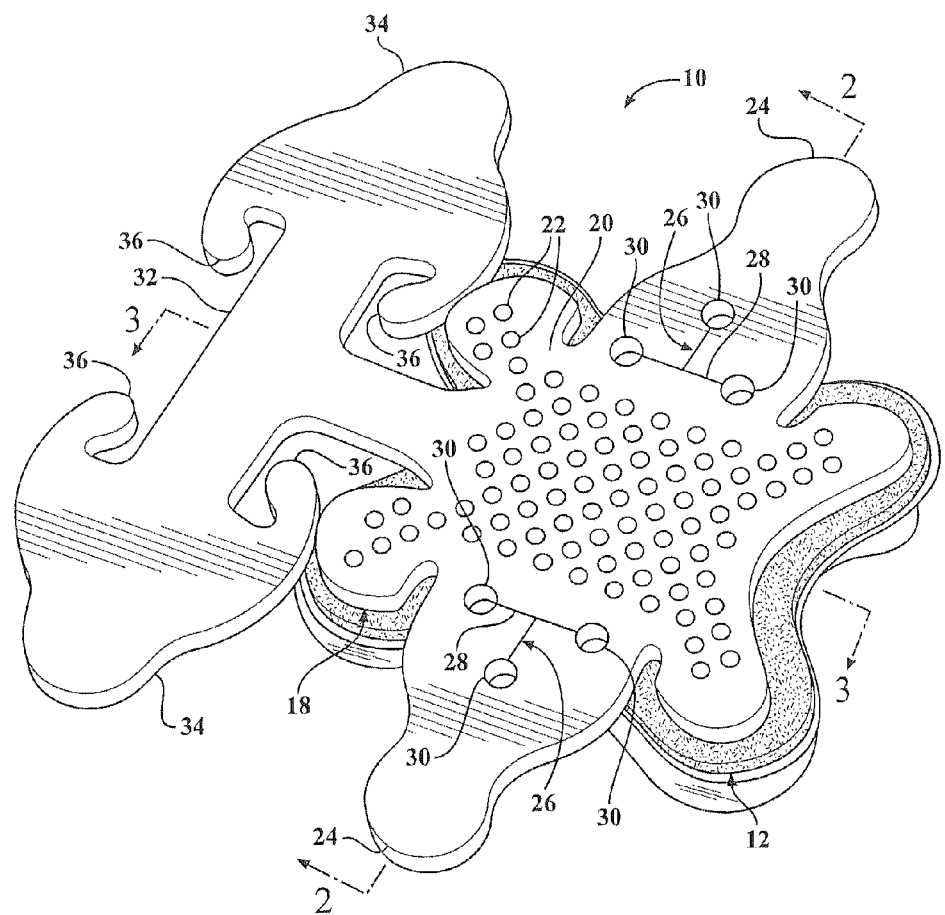
FIG. 1 is a perspective view of an exemplary arrangement of a catheter securement device.

Referring now to the drawings in detail, numeral 10 generally indicates an exemplary catheter securement device. A bottom side of the securement device 10 may be configured to adhere to a patient's skin. The securement device 10 then harnesses the catheter at its bifurcation or trifurcation. Once the catheter tubing is secured by the securement device 10, the securement device provides support for the catheter and greatly decreases unwanted tugging of the catheter from the bifurcation to the catheter insertion site. The securement device 10 also provides comfort by cushioning the catheter as it rests on a patient's body as well as preventing chaffing of a patient's skin. The catheter is also easily removable from the securement device 10, allowing for replacement of the securement device without disturbing the catheter inserted in the insertion site.

Turning first to FIGS. 1 through 3, an exemplary catheter securement device 10 includes a flexible base member 12 having an adhesive side 14 for adherence to a surface such as a patient's skin, and an opposite nonadhesive side 16. The surface of the adhesive side 14 includes an adhesive such as a medical grade adhesive or similar thereon. The base member 12 may be a generally flat, planar member, may be pad-like, and may be made of a foam, fabric, a multi-laminate construction of foam/fabric/film, (which provides functional benefits such as, for example, increased bond strength between the silicon and the base member) or similar material.

An elastomeric anchoring member 18 is mounted on the non-adhesive side of the base member 12. In one exemplary arrangement, anchoring member 18 may be a single unitary piece of material. The anchoring member 18 may be made of any suitable flexible, stretchable elastomeric material such as silicone, polyurethane, high friction rubber, or similar. The material of the anchoring member 18 is preferably silicone. The material of the anchoring member 18 also may be a breathable elastomeric material or alternatively may be a non-breathable elastomeric material. In the case that the material is non-breathable, the anchoring member 18 may include through holes for breathing/ventilation as described in more detail below.

In one exemplary arrangement, the anchoring member 18 integrally includes a body 20 attached to the base member 12 by an adhesive or similar material. The body 20 may include a plurality of ventilation apertures 22 therethrough. The size, arrangement, and number of ventilation apertures 22 is not limited so long as the apertures 22 allow for the passage of air and moisture from the base member 12 through the body 20 without interfering with the attachment of the body 20 to the base member 12 while not allowing adhesive to seep onto body 20. The base member 12 may generally extend beyond the body 20 of the anchoring member 18 such that a peripheral edge of the body is within the outer boundary of the base member. In addition, while the ventilation apertures 22 are desirable in some applications, it is understood that the apertures 22 are not present when it is desired to prevent liquid adhesive from penetrating the securement device.

The base member 12 and the body 20 of the anchoring member 18 are not particularly limited to a certain size and shape. However, the body 20 should be large enough in length and width to provide adequate surface area to receive and support a bifurcated connector portion of the catheter tubing, while also having a small, compact footprint. In the exemplary embodiment shown in FIG. 1, the body 20 is generally rectangular in shape, and may have curved, extended corners for added support. Furthermore, the flexibility of the base member 12 and body 20 allow the securement device 10 to be mounted on almost any location on the human body regardless of bony structures and/or contours.

The anchoring member 18 also integrally includes a pair of opposing pull tabs 24 freely extending outwardly from opposite sides of the body 20. The pull tabs 24 of the anchoring member 18 are free from attachment to the base member 12 in that the pull tabs 24 themselves are not adhered to the base member and are only connected to the base member 12 via their connection to the body 20 of the anchoring member 18. A keeper 26 is disposed in each of the pull tabs 24. The keepers 26 may be located proximate and generally adjacent to the body 20, and each keeper 26 may be at least partially defined by a slit 28 through one of the pull tabs 24. The slit 28 defining the keeper 26 may be T-shaped, and the keeper 26 may further include an aperture 30 at each end of the slit 28. While show as a generally circular aperture, it is understood that any shaped aperture is contemplated within the scope of this application, including, but not limited to, rectangular, square, and elliptical shapes. Pulling each of the pull tabs 24 in a direction away from the body 20 stretches the pull tab 24 and opens the keeper 26 by separating the edges of the slit 28. The circular apertures 30 generally reduce the possibility of the pull tabs tearing upon being stretched and allow the slit to be opened wider. The portion of each pull tab 24 including the keeper 26 may be wider than an outer portion of the pull tab which is intended to be gripped by a user, such as with the user's thumb and index finger.

The anchoring member 18 also integrally includes a T-shaped strap 32 freely extending from the body 20 in a direction generally perpendicular to the orientation of the pull tabs 24. In other words, the strap 32 extends from a side of the body 20 that is adjacent and perpendicular to both the sides of the body 20 from which the pull tabs 24 extend. The strap 32 of the anchoring member 18 is free from attachment to the base member 12 in that the strap 32 itself is not adhered to the base member 12 and is only connected to the base member 12 via its connection to the body 20 of the anchoring member 18. The strap 32 terminates in a pair of opposing heads 34 that are disposed generally parallel to the orientation of the pull tabs 24. The heads 34 may be generally arrow shaped including a portion that is wider than the keeper 26, and each head 34 may include a pair of hooks 36, each hook 36 being cooperable with the keeper 26 to secure the head in the keeper 26. More specifically, each head 34 is cooperable with the most closely neighboring keeper 26. When the strap 32 is manipulated (by bending) so that the heads 34 lay on top of the pull tabs 24, each head 34 is insertable into the adjacent keeper 26. The hooks 36 catch the outer sides of the pull tab 24 to prevent the head 34 from slipping back through the slit 28 of the keeper 26.

The securement device 10 also may include a release liner 38 having a tackless side contacting the adhesive side 14 of the base member 12 to prevent the securement device 10 from adhering to another object prior to its use (i.e., during storage). The release liner 38 generally extends at least to an edge of the base member 12. Optionally, the release liner 38 may include a first piece 40 and a second piece 42. As may be see in FIG. 2, the first and second pieces 40, 42 may be folded such that each of the first and second pieces have tabs 44, 46 formed by the folds 48, 50. One of the pieces can be released from the dressing without tampering with the other piece, which facilitates mounting of the securement device 10 on a surface such as a patient's skin. The side of the securement device 10 with the release liner removed can be placed on the patient's skin while the other side of the securement device 10 with the release liner 38 in place can be held without sticking to the user's thumb and fingers.

Turning to FIGS. 1 and 4 through 8, for purposes of an example, the securement device 10 is shown securing a Foley catheter 52 including a Y-fork connector 54 bifurcating the catheter tubing 56 into an inflation lumen 58 and a drainage lumen 60. The inflation lumen 58 provides a fluid for inflating a balloon 62 of the catheter 52 to hold the catheter in a patient's bladder, while the drainage lumen 60 provides a pathway to drain urine from the patient's bladder. First, a health care provider, herein a nurse for illustrative purposes, inserts the Foley catheter 52 into the patient's bladder through the patient's urethra (which may be referred to as the insertion site). After insertion of the catheter 52, the nurse removes one piece of the release liner 38 that may be present on the adhesive side 14 of the securement device 10 by pulling on the release liner tab. This exposes at least part of the adhesive side 14 of the base member 12, which the nurse mounts on the patient's skin such that the securement device 10 is disposed between the catheter and the patient's skin, and the Y-fork 54 is generally centered on top of the body 20 between the pull tabs 24. The nurse then removes the other piece of the release liner by pulling on the release liner tab to expose the rest of the adhesive side 14 of the base member 12. The base member 12 is then fully adhered to the patient's skin as shown in FIG. 4, and the base member 12 provides a cushioned buffer between the Y-fork 54 of the catheter 52 and the patient's skin. Optionally, it is also understood by those skilled in the art that the catheter 52 may be secured to the securement device 10 prior to adherence of the device to the skin per protocol.

Figures 5, 6:
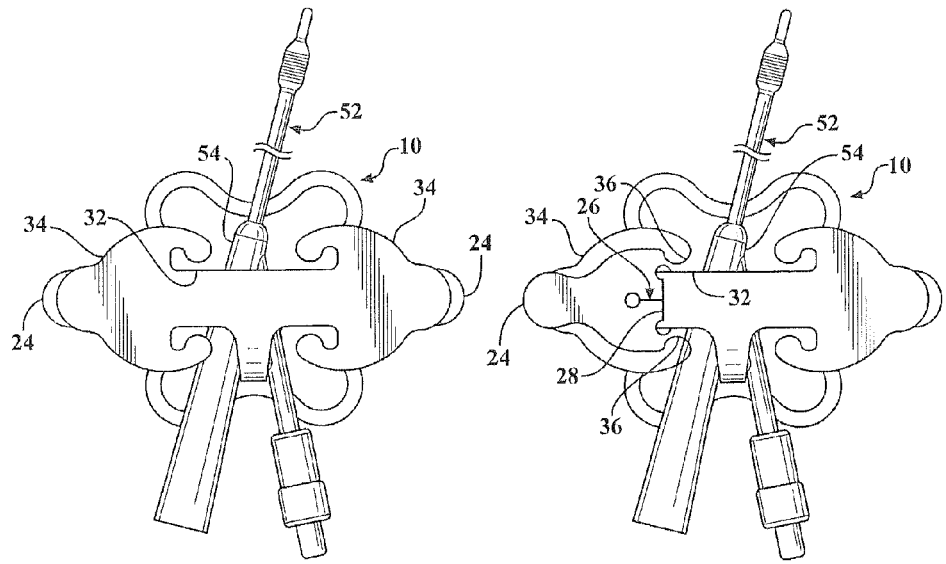
FIG. 5 is an environmental view of the catheter securement device of FIG. 1 adhered to a patient's skin, and illustrating a method of anchoring the catheter in which a strap of the securement device is folded over the catheter.
FIG. 6 is an environmental view illustrating a method of anchoring the catheter in which one end of the strap is inserted into a keeper.
Figures 7, 8:
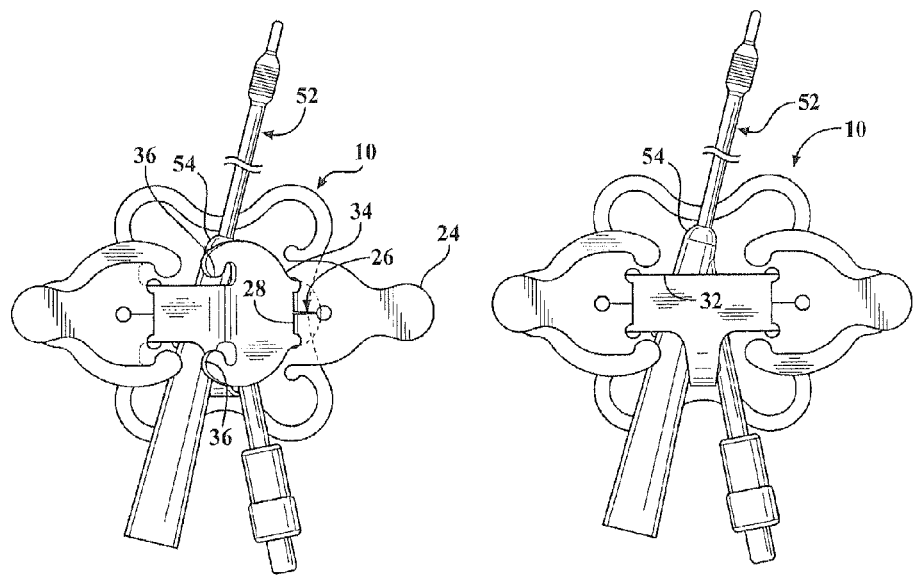
FIG. 7 is an environmental view illustrating a method of anchoring the catheter in which another end of the strap is inserted into a keeper.
FIG. 8 is an environmental view illustrating a catheter fully anchored by the securement device.

At this point, the nurse may hold the catheter 52 in place with one finger and uses his/her other hand to manipulate the strap 32. Optionally, it is understood by those skilled in the art that the catheter may be secured to the securement device 10 prior to adherence of the device to the skin per protocol. In one embodiment, the nurse bends the strap 32 so that it is folded over the body 20 and pull tabs 24 as shown in FIG. 5. In this disposition, the strap 32 straddles the Y-fork 54, and the Y-fork is sandwiched between the body 20 and the strap 32. Also, the heads 34 of the strap 32 lay on top of the pull tabs 24. Next, to secure the strap 32, the nurse uses a free hand to pull one of the pull tabs 24 outwardly and away from the body 20 to expose the slit 28 of the corresponding keeper 26. The adjacent head 34 of the strap 32 is fed through the open slit 28 as shown in FIG. 6, and the nurse then releases the pull tab. As the slit 28 closes around the strap 32, the hooks 36 of the head 34 catch on the pull tab 24, thereby locking the head in the keeper 26. After securing one end of the strap 32, the nurse repeats the same steps with the other end of the strap. Specifically, as shown in FIG. 7, the nurse uses a free hand to pull the other pull tab 24 outwardly and away from the body 20 to open the slit 28 of the corresponding keeper 26. The adjacent head 34 of the strap 32 is fed through the open slit 28, and the nurse then releases the pull tab. As the slit 28 closes around the strap 32, the hooks 36 of the head 34 catch on the pull tab 24, thereby locking the head in the keeper 26. The strap 32 engages the Y-fork 54 of the catheter 52, and the elasticity of the strap provides a constant force against the Y-fork to securely hold the catheter 52 in the securement device 10, as shown in FIG. 8. Due to the material of construction of the anchoring member 18, there is also a significant amount of friction between the strap 32 and the Y-fork 54, which also aids in preventing movement of the catheter 52. Further, the catheter 52 is secured in the securement device 10 without any catheter 52 adhesive coming in contact with the (in contrast to using adhesive tape to secure the catheter), which facilitates later removal of the securement device.

To remove the catheter 52 from the securement device 10, the nurse simply grips one of the pull tabs 24 and pulls it out and upwards away from the body 20 and the patient's skin while pinching the head 34 of the strap 32 and pushing it back through the open slit 28 of the keeper 26. These same steps are repeated for the other pull tab 24 and strap head 34. Since no adhesive ever touches the catheter 52, the catheter cannot become stuck in the securement device 10, and the catheter 52 inserted in the patient's bladder is not disturbed (e.g., not pulled or tugged on) when the catheter is released from the securement device 10. To remove the securement device 10 from the patient's skin, the device can be slowly peeled away from the patient's skin. Alternatively or in addition, alcohol may be used to help break down the adhesive bond between the base member 12 and the skin.

Figure 9:
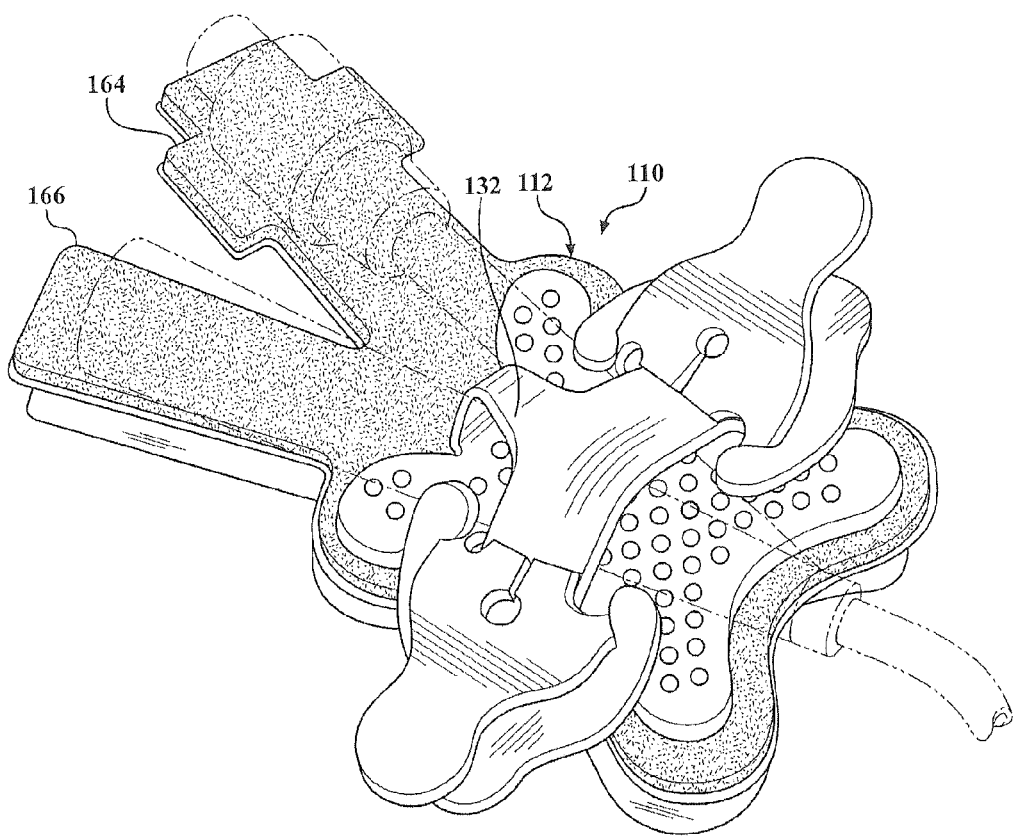
FIG. 9 is a perspective view of an alternative embodiment of a catheter securement device.

In an alternative embodiment of the securement device 110 shown in FIG. 9, the base member 112 includes a pair of arms 164, 166 extending generally in the direction of the strap 132 for providing additional cushioning for the ends of the forked connector of a bifurcated catheter. (shown in phantom) The arms 164, 166 may be shaped to correspond to the shape of the ends of the forked connector. The securement device 110 otherwise has the same structure and features as the first embodiment providing instruction of placing catheter.

Although the invention has been described by reference to specific embodiments, it should be understood that numerous the spirit and scope described. Accordingly, changes may be made within of the inventive concepts it is intended that the invention not be limited to the described embodiments, but that it have the full scope defined by the language of the following claims.

What is claimed is:

1. A catheter securement device comprising:
    a flexible base member having an adhesive side and an opposite non-adhesive side; and
    an elastomeric anchoring member mounted on the non-adhesive side of the base member;
    said anchoring member integrally including a body attached to the base member, a pair of opposing pull tabs freely extending outwardly from the body, a keeper disposed in each of the pull tabs, and a T-shaped strap freely extending from the body, the T-shaped strap terminating in a pair of opposing heads that are disposed generally parallel to the pull tabs;
    wherein pulling the opposing pull tabs opens the keepers for receiving the heads of the T-shaped strap, and the heads being insertable into the keepers for securing a catheter between the anchoring member body and the strap.

2. The catheter securement device of claim 1, wherein the keeper includes a slit.

3. The catheter securement device of claim 2, wherein each keeper comprises a generally T-shaped slit.

4. The catheter securement device of claim 2, wherein the keeper includes an aperture at each end of the slit.

5. The catheter securement device of claim 1, wherein the heads of the strap are generally arrow-shaped.

6. The catheter securement device of claim 1, wherein each head includes a pair of hooks, each hook configured to cooperate with the keeper to secure the head in the keeper.

7. The catheter securement device of claim 1, wherein the base member extends beyond the body of the anchor member.

8. The catheter securement device of claim 1, wherein the base member includes at least one arm extending generally in the direction of the T-shaped strap.

9. The catheter securement device of claim 8, wherein a pair of arms extend generally in the direction of the T-shaped strap.

10. The catheter securement device of claim 9, wherein the arms diverge from one another.

11. The catheter securement device of claim 1, wherein the body of the anchoring member includes a plurality of apertures therethrough.

12. The catheter securement device of claim 1, wherein the anchoring member is made of a flexible, low or high surface energy material.

13. The catheter securement device of claim 1, wherein the anchoring member is made of one of a non-breathable and a breathable elastomeric material.

14. The catheter securement device of claim 1, wherein the base member has a multi-laminate construction.

15. The catheter securement device of claim 1, wherein the T-shaped strap extends from the body in a direction generally perpendicular to the orientation of the pull tabs.

\* \* \* \* \*